United States Patent
Rasetto et al.

(10) Patent No.: US 9,822,383 B2
(45) Date of Patent: Nov. 21, 2017

(54) CONTINUOUS PROCESS FOR TREATING A LIGNOCELLULOSIC BIOMASS

(71) Applicant: Beta Renewables S.p.A., Tortona (IT)

(72) Inventors: Valeria Rasetto, Tortona (IT); Gaia Passerini, Castel San Giovanni (IT); Alberto Anelli, Castiglione d'Adda (IT)

(73) Assignee: Beta Renewables, S.p.A., Tortona (IT)

( * ) Notice: Subject to any disclaimer, the term of this patent is extended or adjusted under 35 U.S.C. 154(b) by 0 days.

(21) Appl. No.: 15/512,089

(22) PCT Filed: Sep. 17, 2015

(86) PCT No.: PCT/EP2015/071278
§ 371 (c)(1),
(2) Date: Mar. 17, 2017

(87) PCT Pub. No.: WO2016/042054
PCT Pub. Date: Mar. 24, 2016

(65) Prior Publication Data
US 2017/0306359 A1    Oct. 26, 2017

(30) Foreign Application Priority Data
Sep. 19, 2014  (IT) .............................. MI2014A1613

(51) Int. Cl.
| | | |
|---|---|---|
| C12P 7/10 | (2006.01) | |
| C13K 1/02 | (2006.01) | |
| C08H 8/00 | (2010.01) | |
| C13K 13/00 | (2006.01) | |
| C08B 37/00 | (2006.01) | |

(52) U.S. Cl.
CPC .................. *C12P 7/10* (2013.01); *C08H 8/00* (2013.01); *C13K 1/02* (2013.01); *C08B 37/0006* (2013.01); *C12P 2201/00* (2013.01); *C13K 13/002* (2013.01)

(58) Field of Classification Search
CPC ........................................................ C12P 7/10
See application file for complete search history.

(56) References Cited

U.S. PATENT DOCUMENTS

| | | | |
|---|---|---|---|
| 4,578,353 A  * | 3/1986 | Assarsson .............. | B01D 3/001 127/36 |
| 8,771,472 B2 | 7/2014 | Beldring et al. | |
| 2008/0054108 A1 | 3/2008 | Matz et al. | |

FOREIGN PATENT DOCUMENTS

| | | | | |
|---|---|---|---|---|
| EP | 1775376 A2 | 4/2007 | | |
| EP | 2610346 A1 | 7/2013 | | |
| IT | EP 2610346 A1 * | 7/2013 | ............... | C09K 3/00 |
| WO | 2010/081476 A1 | 7/2010 | | |

* cited by examiner

*Primary Examiner* — Melvin C Mayes
*Assistant Examiner* — Stefanie Cohen
(74) *Attorney, Agent, or Firm* — Edwin A. Sisson, Attorney at Law, LLC; Jeffrey J. Banyas

(57) ABSTRACT

It is disclosed a continuous process for soaking a ligno-cellulosic biomass stream in an extraction solution comprising water and dissolved water soluble species derived from a previously treated ligno-cellulosic biomass, wherein the soaked ligno-cellulosic biomass stream is optionally rinsed with a rinse solution stream to produce a soaking liquid. The electrical conductivity of the extraction solution and/or the soaking liquid are controlled to a value in a suitable target range by regulating one or more dilution streams.

The disclosed process is useful to remove non-ligno-cellulosic water soluble compounds from the ligno-cellulosic biomass with a low consumption of water.

20 Claims, No Drawings

CONTINUOUS PROCESS FOR TREATING A LIGNOCELLULOSIC BIOMASS

PRIORITIES AND CROSS REFERENCES

This application claims priority from International Patent Application No. PCT/EP2015/071278 filed on 17 Sep. 2015 and Italian Patent Application No. MI2014A001613 filed on 19 Sep. 2014, the teachings of each of which are here-by incorporated by reference in their entirety.

BACKGROUND

Ligno-cellulosic biomasses may be converted to biochemical products and fuels by means of different conversion processes.

Before entering a conversion process, the harvested ligno-cellulosic biomass is usually subjected to an initial processing for rendering the ligno-cellulosic biomass compatible with the conversion process and equipments.

It is desirable to remove inorganic components of the ligno-cellulosic biomass, such as silicates, salts and mineral elements, which are detrimental for the conversion process or equipment.

There is also the need to raise the water content of the raw ligno-cellulosic biomass, which in some cases are received in the conversion plant very dry.

Another problem arising in handling ligno-cellulosic biomasses received in the conversion plant is the presence of external contaminants, such as stones, gravel, sands, sand, dust, clay, metal objects which are present together with the ligno-cellulosic biomasses.

Different equipments and processes have been developed so far for preparing the raw ligno-cellulosic biomass to be further processed.

One approach is to carry out the preparation steps sequentially. As an example, the external contaminants may be first removed from the raw ligno-cellulosic biomass, for instance by means of air floatation equipments, and metallic objects are removed by means of magnetic separation devices. Thereafter, the raw ligno-cellulosic biomass may be treated with water and optionally additives, thereby washing the biomass and increasing its water content. Different methods for washing and/or soaking the biomass are used, typically providing mechanical agitation of the ligno-cellulosic biomass. In this case, an extended biomass handling section is present in the conversion plant, said biomass handling section containing many equipments, usually connected with conveyor belts, to convey the biomass. The distributed approach increases the capital and operative costs, as well as the risk of failure.

A different approach is to integrate the preparation steps into a unique equipment. As an example, in U.S. Pat. No. 8,771,472 an apparatus and a related methods for treating material by cutting, soaking and/or washing of the material are disclosed. The apparatus comprises a receptacle, a discharge element with a vortex generator and pumping means arranged to pump fluid and material from the receptacle towards the vortex generator, wherein the vortex generator and pumping means in combination are adapted to generate a vortex in the form of a conic helix in the fluid extending into the receptacle.

In US2008054108 a pulper having a tank for receiving materials to be shredded and a drive having a rotating hub within the tank id disclosed. A rotor is fixed to the rotating output of the drive, the rotor comprising an annular rotatable hub and a plurality of vanes projecting generally axially from the hub. Each of the vanes has a contour that is swept back from the direction of rotation, at least adjacent the radially outermost portion thereof. The vanes have a side edge facing an axial direction and a plurality of teeth are provided on the side edge of the vanes adjacent the radially outermost portion thereof for providing rapid shredding of material with a reduced energy requirement.

It is desirable that a low amount of water is used for processing of the raw ligno-cellulosic feedstock before entering the conversion process, as the water in excess has to be treated in a waste water facility. Thereby, a trade-off between amount of water used in the treatment and effectiveness of the treatment is desirable.

It is also desirable that the process uses a low amount of energy, which is both thermal energy from heating the process water and electrical energy for supplying mechanical agitation means.

SUMMARY OF THE INVENTION

It is disclosed a process for treating a ligno-cellulosic biomass feedstock, as received in an industrial plant to be converted to biofuels and biochemicals, by using a low amount of water.

The disclosed process achieves many technical objectives: removal of at least a portion of the non-ligno-cellulosic water soluble compounds from the ligno-cellulosic biomass in a short processing time, minimal amount of water sent to waste water treatment, low thermal and electrical energy, as well as the separation of external contaminants from the ligno-cellulosic biomass feedstock.

The disclosed process may be implemented by means of a unique compact equipment integrating all the functionality, thereby reducing the area of the industrial site.

The disclosed process is a continuous process for treating a raw ligno-cellulosic biomass stream, comprising water insoluble contaminants and a ligno-cellulosic biomass comprised of a ligno-cellulosic component, non-ligno-cellulosic water soluble compounds and non-ligno-cellulosic water insoluble compounds, said process comprising the steps of: introducing the raw ligno-cellulosic biomass stream into an extraction vessel containing an extraction solution comprising water and water soluble species and having a first electrical conductivity, wherein at least a portion of the extraction solvent derives from the extraction of a portion of ligno-cellulosic biomass previously treated and contains water soluble species derived from the non-ligno-cellulosic water soluble compounds of the previously treated ligno-cellulosic biomass; releasing in the extraction solution additional water soluble species derived from the non-ligno-cellulosic water soluble compounds of the ligno-cellulosic biomass, to produce a soaked ligno-cellulosic biomass stream; removing the soaked ligno-cellulosic biomass stream from the extraction solution; optionally rinsing the soaked ligno-cellulosic biomass stream with a rinse solution stream comprising water; separating the soaked ligno-cellulosic biomass stream into at least a clean ligno-cellulosic biomass stream and a soaking liquid having an second electrical conductivity and comprising water and water soluble species derived from the non-ligno-cellulosic water soluble compounds of the ligno-cellulosic biomass; diluting the extraction solution with at least a dilution stream comprising water, wherein the flow of the dilution stream and/or the flow of the optional rinse solution stream are regulated to control at least one of the first electrical conductivity and the second electrical conductivity to a target value which is in the range of 0.1 S/m to 5 S/m.

It is also disclosed that the electrical conductivity target value may be in a range selected from the group of 0.2 S/m to 3 S/m, 0.3 S/m to 2 S/m, and 0.5 S/m to 1.5 S/m, at a reference temperature of 25° C.

It is further disclosed that the percent amount of the water soluble species in the extraction solution by weight may be a value in a range selected from the group consisting of 0.25% to 13%, 0.5% to 8%, 0.8% to 5%, and 1.25% to 4%.

It is also disclosed that the water soluble species comprise charged species and neutral species and the ratio by weight of the total amount of charged species to the total amount of neutral species in the extraction solution may be in a range selected from the group consisting of 20:100 to 90:100, 40:100 to 80:100, and 50:100 to 80:100.

It is further disclosed that the percent amount of the water soluble species in the soaking liquid by weight may be a value in a range selected from the group consisting of 0.25% to 13%, 0.5% to 8%, 0.8% to 5%, and 1.25% to 4%.

It is also disclosed that the water soluble species comprise charged species and neutral species and the ratio by weight of the total amount of charged species to the total amount of neutral species in the soaking liquid may be in a range selected from the group consisting of 20:100 to 90:100, 40:100 to 80:100, and 50:100 to 80:100.

It is further disclosed that the soaked ligno-cellulosic biomass stream before separation step e) has a free liquid and the percent amount of the free liquid may less than a value selected from the group consisting of 20%, 10% and 5% by weight of the solid ligno-cellulosic biomass.

It is also disclosed that the soaked ligno-cellulosic biomass stream before separation step e) may be substantially void of the free liquid.

It is further disclosed that at least a portion of the free liquid of the soaked ligno-cellulosic biomass stream may be drained before separation step e).

It is also disclosed that the soaked ligno-cellulosic biomass stream may be separated by means of a compression screw.

It is further disclosed that at least a portion of the water insoluble contaminants may be separated from the ligno-cellulosic biomass in the extraction vessel.

It is also disclosed that a portion of the extraction solution may be discarded from the process, and the total amount of discarded extraction solution per Kg of ligno-cellulosic biomass may be less than a value selected from the group consisting of than 5 l/Kg, 4 l/Kg, 3 l/Kg, 2 l/Kg, and 1 l/Kg.

It is further disclosed that the ratio by weight of the ligno-cellulosic biomass present in the extraction vessel to the extraction liquid in the extraction vessel may be less than a value selected from the group consisting of 1:1000, 1:800, 1:600, 1:400, 1:200, 1:100, 1:70, 1:50, 1:30, 1:20, and 1:10.

It is also disclosed that the temperature of the extraction solution may be in a range selected from the group of 30° C. to 100° C., 40° C. to 99° C., 40° C. to 90° C., and 50° C. to 85° C.

It is further disclosed that the ligno-cellulosic raw biomass stream resides in the extraction vessel for a residence time which may be in a range selected from the group consisting of 30 seconds to 300 minutes, 1 minute to 20 minutes, 2 minutes to 20 minutes, 2 minutes to 15 minutes, and 3 to 10 minutes.

It is also disclosed that the ratio of the raw ligno-cellulosic biomass stream flow in Kg/hour on a dry basis to the optional rinse solution stream in Kg/hour may be less than a value selected from the group consisting of 1:20, 1:15, 1:10, 1:7, 1:5, 1:3, and 1:1.

It is further disclosed that the temperature of the optional rinse solution stream may be greater than or equal to the temperature of the extraction solution.

It is also disclosed that the moisture content of the clean ligno-cellulosic biomass stream may be a value in a range selected from the group consisting of 40% to 75%, 40% to 70%, 45% to 65%, and 45% to 60%.

DETAILED DESCRIPTION

The disclosed process is a continuous process for treating a raw ligno-cellulosic biomass stream as received in an industrial plant to be further converted to biofuels and biochemicals. A raw ligno-cellulosic biomass is one which has been harvested but not yet subjected to a conversion process such as steam or gas explosion. The raw ligno-cellulosic biomass is the ligno-cellulosic biomass as harvested, which has been optionally subjected to preliminary handling and cleaning procedures. Handling procedures are usually done to reduce the transportation costs of the biomass, such as for instance size reduction of the biomass or packing the biomass in bales. Size reduction may be done for instance by grinding, crushing or cutting the biomass. Packing the biomass in bales may reduce the volume needed to transport the biomass, and a certain compression may also be applied to the biomass.

Preferably, the following treatment or conversion process of the ligno-cellulosic biomass stream comprises steps conducted at a pressure which is greater than atmospheric pressure, which is the pressure at which the ligno-cellulosic biomass exits the disclosed process. Thereby, the ligno-cellulosic biomass processed according to the disclosed process is then transferred from a lower pressure to a higher pressure by means of an apparatus such as a plug screw feeder.

The raw ligno-cellulosic biomass stream comprises a ligno-cellulosic biomass and water insoluble contaminants.

For the scope of the disclosed process, the ligno-cellulosic biomass is comprised of a ligno-cellulosic component, non ligno-cellulosic water soluble compounds and non ligno-cellulosic water insoluble compounds.

The ligno-cellulosic component comprises carbohydrates (mainly glucans and xylans) and lignin, which may be then converted to biofuels and biochemicals. Carbohydrates are insoluble polymers of water soluble monomeric sugars (such as glucose and xylose).

The non ligno-cellulosic water soluble compounds comprise compounds naturally present in the ligno-cellulosic biomass different from carbohydrates. When solubilized in water, water soluble species are derived from these compounds by direct solubilization or also by more complex reactions. Water soluble species may be electrically charged neutral species and electrically neutral species. Water soluble charged species may comprise for instance anions and cations of organic and inorganic salts of cations including sodium, calcium, potassium, ammonium, magnesium. Electrical conductivity of a solution increases by increasing the concentration of dissolved charged species. As a general remark, the electrical conductivity depends also on the mobility of charged species. Water soluble neutral species may comprise form instance waxes and extractives and they give a negligible contribution to the electrical conductivity. Thereby, the electrical conductivity of a solution is not affected, or only slightly affected, by the concentration of water soluble neutral species.

Water soluble compounds are defined as follow: an amount of 50 g of ligno-cellulosic biomass is dispersed in 250 mL of distilled water at 65° C. and shaken for 5 minutes. The slurry is filtered with a colander and the liquid fraction is collected and analyzed. Water soluble compounds are the compounds in the liquid fraction having a concentration greater than 0 g/l.

The non ligno-cellulosic water insoluble compounds comprise compounds, such as intrinsic silica present in the ligno-cellulosic biomass, which are not solubilized in water at the conditions of the disclosed process.

The water insoluble contaminants comprise for instance stones, gravel, sands, sand, dust, clay, silica and silicates in general, and metal objects, which are collected with the ligno-cellulosic biomass in harvesting and handling operation of the ligno-cellulosic biomass and it is desirable that they are separated from the ligno-cellulosic biomass before feeding the ligno-cellulosic biomass to downstream devices, which could be damaged. The size of water insoluble contaminants may vary from very small particles, in the sub millimeter range as in the case of sand, to many centimeters, as in the case of stones. They are in general mixed with the ligno-cellulosic biomass and may adhere on the surface of the ligno-cellulosic biomass or be present in bundles of the ligno-cellulosic biomass. In these cases, separation from the ligno-cellulosic biomass may be difficult.

Preferably, the percent amount of the contaminants in the ligno-cellulosic raw biomass stream is less than a 10%, 5%, 3%, and 1% on dry weight basis.

Ligno-cellulosic biomasses are described in details in a following section.

Even if any kind of ligno-cellulosic biomass may be treated according to the disclosed process, a preferred feedstock is a ligno-cellulosic biomass comminuted in chips, wherein the chips are characterized by a low bulk density. The bulk density is defined as the mass of many particles of the material divided by the total volume they occupy. The total volume includes particle volume, inter-particle void volume, and internal pore volume. Bulk density is not an intrinsic property of a material; it can change depending on how the material is handled. The bulk density is determined according to the standard ASABE S 269.4 DEC91 (ASABE standards, American Society of Agricultural and Biological Engineers), which defines methods and procedures for measuring unit density, bulk density, durability, and moisture content of various densified products composed mainly of forage, woody crops, or other fibrous and non-fibrous material for bulk handling in the feed and non-feed industries. The bulk density may be less than 300 kg/m$^3$, preferably less than 250 kg/m$^3$, more preferably less than 200 kg/m$^3$, even more preferably less than 150 kg/m$^3$, even yet more preferably less than 100 kg/m$^3$, most preferably less than 75 kg/ms, being less than 50 kg/m$^3$ the even most preferred value. The bulk density may be greater than 10 kg/m$^3$, preferably greater than 15 kg/m$^3$, more preferably greater than 20 kg/m$^3$. The bulk density is measured at a moisture content of 10%.

Even if the disclosed process may feed comminuted ligno-cellulosic biomass composed by chips of any shape, the advantages are evident in the case of elongated chips. The comminuted ligno-cellulosic feedstock may be characterized by the mean aspect ratio of the chips, wherein the aspect ratio of a chip is defined as the ratio of its longest size and the mean size in the section transversal to the longest size. The average is done on a sampling of the feedstock having a statistical relevance. As an example, in the case of wheat straw, the chip may be as long as some tens of centimeter and the mean transversal size is typically a few millimeters. The mean aspect ratio may be more than 3:1, preferably more than 5:1, more preferably more than 10:1, even more preferably more than 15:1, even yet more preferably more than 20:1, most preferably more than 30:1, being more than 40:1 the even most preferred value.

Preferably, the ligno-cellulosic feedstock is selected from the group consisting of switchgrass, *Mischantus*, *Arundo Donax*, sugar cane straw, bagasse, wheat straw, barley straw, and rice straw.

According to one aspect of the invention, the ligno-cellulosic feedstock is treated in a dirty extraction solution to solubilize at least a portion of the water soluble non-ligno-cellulosic compounds, the dirty extraction solution comprising dissolved water soluble species derived from a previously aliquot of the treated ligno-cellulosic biomass. Stated in other words, the water soluble species derived from the ligno-cellulosic biomass stream are accumulated in the extraction solution. Moreover, also fine particles of water insoluble contaminants are accumulated in the extraction solution, which appears dark brown-colored. Inventors have found that by taking as a quality or control parameter the electrical conductivity of the dirty stream or streams in one or more points of the treatment process, water consumption may be reduced or minimized. The electrical conductivity of the extraction solution, or a soaking liquid stream extracted from the soaked ligno-cellulosic biomass, or both, may be used to regulated the flows of the liquid flows entering and exiting the disclosed process. Inventors have found that the electrical conductivity is a representative parameters of the solubilization process, that is of the total concentration of all the water soluble species, even if it is affected only by the concentration of the dissolved water soluble charged species.

According to another aspect of the invention, the water insoluble contaminants are separated from the ligno-cellulosic biomass by means of apparent mass density, thereby with no or minimal use of external mechanical energy.

According to a further aspect of the invention, the ligno-cellulosic biomass is first treated in an great amount of a dirty extraction solution, having a high concentration of water soluble species, and then rinsed with a low flow of a clean rinse solution stream, which is preferably used to dilute the extraction solution, thereby with a minimal use of net clean water needed for running the whole process.

The disclosed process is a continuous process, wherein the raw ligno-cellulosic biomass stream is introduced in an extraction vessel containing an extraction solution to remove at least a portion of the non-ligno-cellulosic water soluble compounds from the ligno-cellulosic biomass by solubilization into the extraction solution. In order for the disclosed process to be continuous, it is not necessary that the raw ligno-cellulosic biomass stream is continuously introduced into the extraction vessel, but it can be introduced at steady aliquots or pulses. Thus there are moments when there is no raw ligno-cellulosic biomass entering the extraction vessel. But, over time, the total mass introduced into the extraction vessel equals the total mass removed from the extraction vessel. One distinguishing feature between a continuous and a batch process is that, in a continuous process, the separation step is occurring or progressing at the same time that either the raw ligno-cellulosic biomass is introduced into the extraction vessel and/or the soaked ligno-cellulosic feedstock stream is removed from the extraction vessel. Another way to state this is that the separation in the extraction vessel occurs while simultaneously, or at the same time, removing the soaked ligno-cellulosic feedstock stream from the extraction vessel. Such removal is done in a continuous manner which includes an aliquot or pulse removal.

The extraction vessel may be of any of size and shape suitable for the scope of the disclosed process. The extraction vessel may be an open vessel, with a free surface of the extraction solution exposed to the external environment, or a closed vessel, with a cover to insulate the extraction solution from the external environment.

Preferably, the extraction vessel has the shape of a pool, with an elongated horizontal section, with a main dimension, or length, which may be between 2 m and 100 m, preferably between 4 m and 80 m, even more preferably between 4 m and 40 m.

The horizontal section of the extraction vessel may have a rectangular-like shape, which may be modified for instance for orienting the ligno-cellulosic biomass toward a specific region of the extraction vessel or preventing accumulation of the ligno-cellulosic biomass in some region of the extraction vessel.

The height of the separation pool may be from 10 cm to 10 nm, preferably between 50 cm and 6 m, more preferably between 1 m and 5 m, and most preferably between 2 m and 4 m. The height of the extraction vessel may not be uniform, and in this case the height corresponds to the minimum height of the vessel.

The extraction solution contained in the extraction vessel comprises water and water soluble compounds which have been solubilized by the treatment of a previous aliquot of the ligno-cellulosic biomass stream.

The extraction liquid may fill completely the extraction vessel, as in the case of a closed vessel, or it may partly fill the extraction vessel.

Preferably, the height of the extraction liquid is sufficient to separate the water insoluble contaminants according to the disclosed process.

In the case that the raw ligno-cellulosic biomass stream is a straw compacted in bales, the bales are preferably disaggregated for introducing the loose raw ligno-cellulosic biomass stream into the extraction vessel.

The raw ligno-cellulosic biomass stream is preferably introduced into the extraction vessel as a dry biomass, meaning that no free liquid is present in the incoming stream. The moisture content is preferably less than 50%, more preferably less than 30%, even more preferably less than 20%, and most preferably less than 10%. In another embodiment, the raw ligno-cellulosic biomass stream is introduced into the extraction vessel as a slurry stream, mixed with a liquid comprising water.

If the extraction vessel is open-type, the raw ligno-cellulosic biomass stream is preferably introduced into the extraction vessel by gravity through the free surface of the extraction liquid, for instance by means of a conveyor belt, and it may be spread on a wide portion or, preferably, on a limited portion of the surface of the extraction solution.

The raw ligno-cellulosic biomass stream may be introduced by forced conveying, for instance by means of a screw conveyor, below the maximum height of the extraction solution, which corresponds to the free surface of the extraction liquid in the case that the extraction vessel is open.

A portion of the non ligno-cellulosic water soluble compounds contained in the ligno-cellulosic biomass are solubilized in the extraction solution, thereby adding new water soluble species to the extraction solution. A small amount of the carbohydrates of the ligno-cellulosic component may be also solubilized to soluble sugars in the extraction solution, depending on the temperature of the extraction solution and the residence time of the ligno-cellulosic biomass in the extraction vessel. Preferably, the process conditions are such that the most portion of the water soluble compounds are solubilized in the extraction water while no significant solubilization of the carbohydrates occurs.

Mechanical agitation may be provided to further improve solubilization of the water soluble compounds.

The solubilization of the non ligno-cellulosic water soluble compounds is enhanced at high temperature of the extraction solution. The temperature of the extraction solution may be between 30° C. and 100° C., preferably between 40° C. and 99° C., more preferably between 40° C. and 90° C., and most preferably between 50° C. and 85° C. Preferably, the temperature is selected to not solubilize the insoluble carbohydrates of the ligno-cellulosic biomass. A fluid at a temperature higher than the extraction solution temperature circulating in a piping system in thermal contact with the extraction solution may be used to heat the extraction solution at the desired temperature.

The residence time of the ligno-cellulosic biomass in the extraction solution may be between 30 seconds and 300 minutes, preferably between 1 minute and 20 minutes, more preferably between 2 minutes and 20 minutes, even more preferably between 2 minutes and 15 minutes, and most preferably between 3 and 10 minutes. The residence time may be evaluated by tracing a portion of the ligno-cellulosic biomass in the extraction vessel.

The solubilization step is preferably conducted in an excess of extraction solution with respect to the amount of ligno-cellulosic biomass present in the extraction vessel. Preferably the ratio by weight of the ligno-cellulosic biomass present in the extraction vessel to the extraction liquid in the extraction vessel is less than a value selected from the group consisting of 1:1000, 1:800, 1:600, 1:400, 1:200, 1:100, 1:70, 1:50, 1:30, 1:20, and 1:10. The amount of extraction solution in the extraction vessel is controlled by regulating the flows of streams entering and exiting the extraction vessel.

The extraction solution comprises a total amount of water soluble species which have been accumulated while running the disclosed continuous process. The percent amount of the water soluble species in the extraction solution may be a value in a range selected from the group consisting of 0.25% to 13%, preferably of 0.5% to 8%, more preferably of 0.8% to 5%, and most preferably of 1.25% to 4%.

As the water soluble species comprise charged species and neutral species, the extraction solution may be characterized by the ratio by weight of the total amount of charged species to the total amount of neutral species, which may be in a range selected from the group consisting of 20:100 to 90:100, preferably of 40:100 to 80:100, and most preferably of 50:100 to 80:100.

The electrical conductivity of the extraction solution varies with the concentration of the water soluble charged species in the extraction solution and it is not affected by the concentration of the water soluble neutral species. Thereby, two extraction solutions having the same concentration of water soluble charged species but different concentrations of neutral species will have the same electrical conductivity. As the extraction solution is removed from the separation vessel in an unselective way with respect to the electrical charge of the water soluble species, that is preventing the accumulation of a particular type of species, inventors have found that the electrical conductivity may be used for representing the total concentration of the water soluble species, thereby providing a parameter for controlling the quality of the extraction solution.

The electrical conductivity of the extraction solution is controlled to a target value in a suitable target range. If the electrical conductivity would be less than the lower limit of the target range, the water soluble species in the extraction vessel would be too much diluted indicating an excessive water consumption. On the other hand, if the electrical conductivity would be higher than the upper limit, the extraction solution would be too much dirt and the release of additional water soluble species may be less effective. It is important to specify that, while conducting the disclosed process continuously, there may be intervals of time in which the electrical conductivity of the extraction solution is outside the target range. That is, there may be aliquots of the ligno-cellulosic biomass which are treated in an extraction solution having an electrical conductivity outside the target range. The electrical conductivity is controlled to a mean value in the target range over a time period which is greater than the residence time of the ligno-cellulosic biomass in the extraction vessel.

The electrical conductivity of the extraction solution is in a range of 0.1 S/m to 5 S/m, preferably of 0.2 S/m to 3 S/m, more preferably of 0.3 S/m to 2 S/m, and most preferably of 0.5 S/m to 1.5 S/m. Being the electrical conductivity strongly dependent on the temperature, the preferred ranges are defined at the reference temperature of 25° C. The range of the electrical conductivity at the extraction solution temperature may be easily determined according to a reference measurement of the electrical conductivity at the reference temperature.

A wide variety of instrumentation is commercially available for measuring the electrical conductivity. In general, there are two types of cell, the classical type with flat or cylindrical electrodes and a second type based on induction. Many commercial systems offer automatic temperature correction. The conductivity may be measured by inserting the probe in the extraction vessel or in an aliquot of the extraction solution removed from the extraction vessel. The electrical conductivity may be measured continuously or intermittently.

The electrical conductivity of the extraction solution is controlled around a target value in the preferred ranges by regulating the flow of one or more dilution streams added to the extraction solution, having a concentration of water soluble species which is lower than the concentration of the water soluble species in the extraction solution. A stream of clean water may be added to the extraction solution from an external water source. Other dilution streams may be obtained by recycling internal streams of the process. The different streams may be added to the extraction solution from different inlets, or combined together to form a unique stream before being inserted into the extraction solution. The temperature of the dilution stream or streams may be greater that the temperature of the extraction solution to increase or maintain the temperature of the extraction solution.

A stream of the extraction solution is discarded from the extraction vessel and it may also be regulated to control the electrical conductivity in the target range. The stream may be removed from a dedicated outlet or together with the soaked ligno-cellulosic biomass removed from the extraction vessel. The process may be characterized by the total amount of extraction solution discarded from the process, in all form including sludge, for treating a Kg of ligno-cellulosic biomass on a dry basis, The total amount of extraction solution discarded from the process is preferably less than 5 l/Kg, more preferably less than 4 l/Kg, even more preferably less than 3 l/Kg, even yet more preferably less than 2 l/Kg, and most preferably less than 1 l/Kg per Kg of ligno-cellulosic biomass.

The stream of the extraction solution discarded from the process may be sent to a waste water treatment facility.

The electrical conductivity of the extraction solution may be maintained in the desired range by means of an automatic system, preferably a computer-controlled system, which regulates the flow of the dilution stream or streams.

In a preferred embodiment, the water insoluble components of the raw ligno-cellulosic biomass stream are separated according to their apparent mass densities in the extraction solution. It is noted that the apparent mass density in the extraction solution is different from the bulk density as defined by reference standard ASAE 269.4, because the extraction solution fills interstitial voids and it may also penetrate at least partially into the pores of the biomass. The apparent mass density in the extraction solution may be defined according to the ASAE 269.4, with the exception that the biomass is inserted into a container filled with extraction solution instead of air. The raw ligno-cellulosic biomass in the extraction vessel may comprise bundles of ligno-cellulosic biomass, wherein particles of insoluble contaminants are included. For the scope of the disclosed separation, the bundle is a distinct unit which is separated according to its own apparent mass density. The water insoluble components, including bundles of ligno-cellulosic biomass, are thereby separated by buoyancy into at least a waste stream, deposited at the bottom of the extraction vessel, and comprising at least the majority of the water insoluble contaminants, and a soaked ligno-cellulosic biomass stream, floating at the top of the extraction vessel, and comprising the majority of the ligno-cellulosic biomass. The waste stream may further comprise a portion of the ligno-cellulosic biomass, which is preferably less than 15%, more preferably less than 10%, even more preferably less than 5% and most preferably less than 3% by weight on a dry basis of the ligno-cellulosic biomass entering the extraction vessel. The soaked ligno-cellulosic biomass stream may further comprise a portion of the water insoluble contaminants, which is preferably less than 15%, more preferably less than 10%, even more preferably less than 5% and most preferably less than 3% by weight on a dry basis of the water insoluble contaminants entering the extraction vessel.

Separation of the water insoluble components may be promoted by mechanical agitation of the raw ligno-cellulosic biomass in the extraction vessel, for instance by means of paddle wheels. Separation may also be promoted by gas floatation by injecting gas bubbles into the extraction solution. The small bubbles adhere to the suspended bundles causing the suspended bundles to float to the surface of the extraction solution. Preferred gas is air.

The waste stream deposited at the bottom of the extraction vessel may be removed by means of mechanical means such as a paddle conveyor belt, or by gravity.

The soaked ligno-cellulosic biomass stream may be conveyed toward an outlet region of the extraction vessel by means of a mechanical system, which may comprise a paddle conveyor belt, or a paddle wheel, or both. A net flow of the extraction solution in the extraction vessel may also be used. In this case, the extraction solution flows from an inlet of the extraction solution to an outlet of the extraction solution, wherein it is removed and recirculated back into the extraction vessel from the inlet.

Passive means, such as fixed barriers may be present in the extraction vessel to orient and accumulate the soaked ligno-cellulosic biomass stream toward the outlet region of the soaked ligno-cellulosic biomass stream, preventing the accumulation of the biomass in dead zones of the extraction vessel.

The soaked ligno-cellulosic biomass stream is removed from the extraction vessel, preferably from an outlet of the soaked ligno-cellulosic biomass stream positioned in or close to the outlet region of the extraction vessel. The soaked ligno-cellulosic biomass is removed from the extraction vessel in the form of a diluted slurry stream with a portion of the extraction solution, and it is preferably drained to separate a dirty liquid stream comprising at least a portion of the free liquid of the soaked ligno-cellulosic biomass slurry stream. The dirty liquid stream comprises water and non-ligno-cellulosic water soluble compounds, and may further comprise some insoluble components. Separation occurs preferably under the action of gravity and the separated dirty liquid stream, which is approximately at the same temperature of the extraction solution in the extraction vessel, may be introduced into the extraction vessel, with or without any further processing step. Stated in another way, preferably there is a continuous draining of the liquid dirty stream into the extraction vessel.

A preferred way to remove the soaked ligno-cellulosic biomass stream from the extraction vessel is by means of a mechanical removal system connected to the outlet of the soaked ligno-cellulosic biomass stream and extending to an upper position of the extraction vessel with respect to the gravity. Preferably, the mechanical removal system comprises a conveyor belt, more preferably a paddle conveyor system, which extracts the soaked ligno-cellulosic biomass slurry stream from an outlet zone of the extraction vessel and drains the dirty liquid stream while lifting the soaked ligno-cellulosic feedstock stream to the upper position. Holes may be suitable located on the conveyor belt to promote draining of the free liquid.

In an embodiment, all the dirty liquid stream is reintroduced into the extraction vessel. In another embodiment it is reintroduced at least 50% by weight, more preferably at least 60%, even more preferably at least 70% and most preferably at least 80% portion of the dirty liquid stream. One reason to remove a portion of the dirty liquid stream from the process is to prevent the excessive accumulation of the water soluble species derived from the non-ligno-cellulosic water soluble compounds in the extraction solution.

As draining removes most the free liquid in the soaked ligno-cellulosic biomass slurry stream, the soaked ligno-cellulosic biomass stream after draining has a low content of free liquid, which is preferably less than 20%, more preferably less 10%, and most preferably less than 5% weight of the soaked ligno-cellulosic biomass stream after draining on wet basis.

In a preferred embodiment, the soaked ligno-cellulosic biomass stream after draining is substantially void of free liquid, that is the free liquid is less than 1% by weight. Free liquid is the liquid which is separated by decanting an aliquot of the soaked ligno-cellulosic stream after draining in a decanter for 1 hour.

As the ligno-cellulosic biomass is treated with the dirty extraction solution containing accumulated water soluble species, in a preferred embodiment the soaked ligno-cellulosic biomass stream is rinsed with a rinse solution stream, preferably while draining the dirty liquid stream from the soaked ligno-cellulosic biomass stream. The rinse solution stream comprises water and it is in general more clean than the extraction solution. In this way, at least a portion of water soluble species which have been solubilized but may adhere to the ligno-cellulosic component are removed from the soaked ligno-cellulosic biomass stream. In this case, the dirty liquid stream comprises the drained rinse solution and has a concentration of water soluble species which is less than the concentration of water soluble species in the extraction solution. The dirty liquid stream may be introduced into the extraction vessel as a dilution stream. In one embodiment, the dirty liquid stream is the unique dilution stream used to dilute the extraction solution.

In a preferred embodiment, the soaked ligno-cellulosic biomass stream is rinsed in a limited flow of rinsed solution stream, thereby the discloses process minimize the total amount of water needed for treating the ligno-cellulosic biomass. The ratio of the flow of the soaked ligno-cellulosic feedstock stream in Kg/hour on a dry basis to the flow of the rinse solution stream in Kg/hour is less than 1:20, preferably less than 1:15, more preferably less than 1:10, even more preferably less than 1:7, 1:5, even yet more preferably less than 1:3, and most preferably less than 1:1.

Preferably the rinse solution stream is injected in a counter-flow configuration with respect to the soaked ligno-cellulosic biomass stream, and it may be injected through one or more injection points while the soaked ligno-cellulosic biomass stream is conveyed by the mechanical removal system.

The rinse solution stream may be at a temperature between 30° C. and 100° C., preferably between 40° C. and 99° C., more preferably between 40° C. and 90° C., and most preferably between 50° C. and 85° C.

In an embodiment, the temperature of the rinse solution stream is greater than or equal to the temperature of the extraction liquid and the dirty liquid stream may be introduced into the extraction vessel so as to heat the extraction solution.

The soaked ligno-cellulosic biomass stream is rinsed for a rinsing time which is a value in a range selected from the group consisting of 30 seconds to 300 minutes, 1 minute to 20 minutes, 2 minutes to 20 minutes, 2 minutes to 15 minutes, and 3 to 10 minutes. The soaked ligno-cellulosic biomass stream may be a significant portion of the residence time of the ligno-cellulosic biomass in the separation pool. Preferably, the rinse time is in a range between 1% and 80%, more preferably between 5% and 70%, even more preferably between 10% and 60%, and most preferably between 20% and 50% of the residence time. Thereby, an additional portion of the non-ligno-cellulosic water soluble compounds may be further solubilized during rinsing and removed from the soaked ligno-cellulosic biomass stream.

Even if the soaked ligno-cellulosic biomass stream contains few or no free liquid, the moisture content is still high, being the ligno-cellulosic biomass soaked with the extraction solution. The moisture content may be in the range 70% to 95%, preferably of 70% to 90%, more preferably of 75% to 95%, and most preferably of 75% to 90%.

The soaked ligno-cellulosic biomass stream is separated into at least a soaking liquid stream and a clean ligno-cellulosic biomass stream preferably by means of a continuous compression device. A preferred device is a compression screw, located in a cylindrical housing having an annular filter screen to remove liquids while continuously conveying the clean ligno-cellulosic biomass stream. The moisture content of the clean ligno-cellulosic biomass stream is in the range of 40% to 75%, preferably of 40% to 70%, more preferably of 45% to 65%, and most preferably of 45% to 60%. The soaking liquid comprises water and additional water soluble species, which were mainly absorbed with the soaked ligno-cellulosic biomass. The soaking liquid may further comprise a small portion of solid ligno-cellulosic biomass suspended within the liquid.

Inventors found that the electrical conductivity of the soaking liquid is representative of the effectiveness of the process in solubilizing the non-ligno-cellulosic water soluble compounds and it may be used as a quality or control parameter to regulate the flow of the dilution stream or streams, in order to reduce the amount of net water used in the process.

The electrical conductivity of the soaking liquid is controlled to a target value which is in a suitable target range, with the same considerations as in the case of the extraction solution. In particular, the electrical conductivity is controlled to a mean value in the target range over a time period which is greater than the residence time of the ligno-cellulosic biomass in the extraction vessel.

The electrical conductivity of the soaking liquid is in a range of 0.1 S/m to 5 S/m, preferably of 0.2 S/m to 3 S/m, more preferably of 0.3 S/m to 2 S/m, and most preferably of 0.5 S/m to 1.5 S/m. Being the electrical conductivity strongly dependent on the temperature, the preferred ranges are defined at the reference temperature of 25° C.

The total amount of the water soluble species in the soaking liquid by weight may be a value in a range selected from the group consisting of 0.25% to 13%, preferably of 0.5% to 8%, more preferably of 0.8% to 5%, and most preferably of 1.25% to 4%.

As the water soluble species comprise charged species and neutral species, also the soaking liquid may be characterized by the ratio by weight of the total amount of charged species to the total amount of neutral species, which may be in a range selected from the group consisting of 20:100 to 90:100, preferably of 40:100 to 80:100, and more preferably of 50:100 to 80:100.

The electrical conductivity of the soaking liquid may be the unique control parameter, or it can be used as an additional parameter. In the latter case, the target value of the soaking liquid conductivity may be different from the target value of the extraction solution conductivity, and the target value of the soaking liquid conductivity is preferably greater than the target value of the extraction solution conductivity. In yet another embodiment, the target value of the soaking liquid conductivity is in a first range and the target value of the soaking liquid conductivity is in a second range, and the first range and the second range are different. The electrical conductivity of both the extraction solution and the soaking liquid are controlled by regulating the flow of dilution stream or streams.

The soaking liquid may be reintroduced into the extraction vessel, eventually after removing suspended solids. The clean ligno-cellulosic biomass stream may then feed a plug screw feeder to enter a conversion process at pressurized conditions to produce biofuels and biochemicals.

Ligno-Cellulosic Biomass

In general, a ligno-cellulosic feedstock, indicated also as ligno-cellulosic biomass can be described as follows:

Apart from starch, the three major constituents in plant biomass are cellulose, hemicellulose and lignin, which are commonly referred to by the generic term lignocellulose. Polysaccharide-containing biomasses as a generic term includes both starch and ligno-cellulosic biomasses. Therefore, some types of feedstocks can be plant biomass, polysaccharide containing biomass, and ligno-cellulosic biomass which may or may not contain starch.

Polysaccharide-containing biomasses according to the present invention include any material containing polymeric sugars e.g. in the form of starch as well as refined starch, cellulose and hemicellulose.

Relevant types of ligno-cellulosic feedstock for deriving the claimed invention may include biomasses derived from agricultural crops selected from the group consisting of starch containing grains, refined starch; corn stover, bagasse, straw e.g. from rice, wheat, rye, oat, barley, rape, sorghum; softwood e.g. *Pinus sylvestris, Pinus* radiate; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like. Although the experiments are limited to a few examples of the enumerated list above, the invention is believed applicable to all the member of the list.

In one embodiment, the ligno-cellulosic biomass feedstock used in the process is from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass leaves are usually alternate, distichous (in one plane) or rarely spiral, and parallel-veined. Each leaf is differentiated into a lower sheath which hugs the stem for a distance and a blade with margins The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchard grass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indian grass, bermuda grass and switch grass.

One classification of the grass family recognizes twelve subfamilies: These are 1) anomochlooideae, a small lineage of broad-leaved grasses that includes two genera (Anomochloa, Streptochaeta); 2) Pharoideae, a small lineage of grasses that includes three genera, including Pharus and Leptaspis; 3) Puelioideae a small lineage that includes the African genus Puelia; 4) Pooideae which includes wheat, barley, oats, brome-grass (Bronnus) and reed-grasses (Calamagrostis); 5) Bambusoideae which includes bamboo; 6) Ehrhartoideae, which includes rice, and wild rice; 7) Arundinoideae, which includes the giant reed and common reed; 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the muhly grasses (Muhlenbergia, ca. 175 species); 10) Panicoideae including panic grass, maize, sorghum, sugar cane, most millets, fonio and bluestem grasses; 11) Micrairoideae and 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Another ligno-cellulosic biomass feedstock may be woody plants or woods. A woody plant is a plant that uses wood as its structural tissue. These are typically perennial plants whose stems and larger roots are reinforced with wood produced adjacent to the vascular tissues. The main stem, larger branches, and roots of these plants are usually covered by a layer of thickened bark. Woody plants are usually either trees, shrubs, or lianas. Wood is a structural cellular adaptation that allows woody plants to grow from above ground stems year after year, thus making some woody plants the largest and tallest plants.

These plants need a vascular system to move water and nutrients from the roots to the leaves (xylem) and to move sugars from the leaves to the rest of the plant (phloem). There are two kinds of xylem: primary that is formed during primary growth from procambium and secondary xylem that is formed during secondary growth from vascular cambium.

What is usually called "wood" is the secondary xylem of such plants.

The two main groups in which secondary xylem can be found are:

1) conifers (Coniferae): there are some six hundred species of conifers. All species have secondary xylem, which is relatively uniform in structure throughout this group. Many conifers become tall trees: the secondary xylem of such trees is marketed as softwood.

2) angiosperms (Angiospermae): there are some quarter of a million to four hundred thousand species of angiosperms. Within this group secondary xylem has not been found in the monocots (e.g. Poaceae). Many non-monocot angiosperms become trees, and the secondary xylem of these is marketed as hardwood.

The term softwood is used to describe wood from trees that belong to gymnosperms. The gymnosperms are plants with naked seeds not enclosed in an ovary. These seed "fruits" are considered more primitive than hardwoods. Softwood trees are usually evergreen, bear cones, and have needles or scale like leaves. They include conifer species e.g. pine, spruces, firs, and cedars. Wood hardness varies among the conifer species.

The term hardwood is used to describe wood from trees that belong to the angiosperm family. Angiosperms are plants with ovules enclosed for protection in an ovary. When fertilized, these ovules develop into seeds.

The hardwood trees are usually broad-leaved; in temperate and boreal latitudes they are mostly deciduous, but in tropics and subtropics mostly evergreen. These leaves can be either simple (single blades) or they can be compound with leaflets attached to a leaf stem. Although variable in shape all hardwood leaves have a distinct network of fine veins. The hardwood plants include e.g. Aspen, Birch, Cherry, Maple, Oak and Teak.

Therefore, in one embodiment, a suitable ligno-cellulosic biomass may be selected from the group consisting of the grasses and woods. In one embodiment, ligno-cellulosic biomass can be selected from the group consisting of the plants belonging to the conifers, angiosperms, Poaceae and families. Another preferred ligno-cellulosic biomass may be that biomass having at least 10% by weight of it dry matter as cellulose, or more preferably at least 5% by weight of its dry matter as cellulose.

The invention claimed is:

1. A continuous process for treating a raw ligno-cellulosic biomass stream, comprising water insoluble contaminants and a ligno-cellulosic biomass comprised of a ligno-cellulosic component, non-ligno-cellulosic water soluble compounds and non-ligno-cellulosic water insoluble compounds, said process comprising the steps of:
   a. introducing the raw ligno-cellulosic biomass stream into an extraction vessel containing an extraction solution comprising water and water soluble species and having a first electrical conductivity, wherein at least a portion of the extraction solvent derives from the extraction of a portion of ligno-cellulosic biomass previously treated and contains water soluble species derived from the non-ligno-cellulosic water soluble compounds of the previously treated ligno-cellulosic biomass;
   b. releasing into the extraction solution additional water soluble species derived from the non-ligno-cellulosic water soluble compounds of the ligno-cellulosic biomass, to produce a soaked ligno-cellulosic biomass stream;
   c. removing the soaked ligno-cellulosic biomass stream from the extraction solution;
   d. optionally rinsing the soaked ligno-cellulosic biomass stream with a rinse solution stream comprising water;
   e. separating the soaked ligno-cellulosic biomass stream into at least a ligno-cellulosic biomass stream and a soaking liquid having a second electrical conductivity and comprising water and water soluble species derived from the non-ligno-cellulosic water soluble compounds of the ligno-cellulosic biomass;

f. diluting the extraction solution with at least a dilution stream comprising water, wherein the flow of the dilution stream is regulated to control at least one of the first electrical conductivity and the second electrical conductivity to a target value which is in the range of 0.1 S/m to 5 S/m.

2. The process of claim 1, wherein the target value is in a range of 0.2 S/m to 3 S/m, at a reference temperature of 25° C.

3. The process of claim 1, wherein the percent amount of the water soluble species by weight in the extraction solution is a value in a range of 0.25% to 13%.

4. The process of claim 3, wherein the water soluble species comprise charged species and neutral species and the ratio by weight of the total amount of charged species to the total amount of neutral species in the extraction solution is in a range of 20:100 to 90:100.

5. The process of claim 1, wherein the percent amount of the water soluble species by weight in the soaking liquid is a value in a range of 0.25% to 13%.

6. The process of claim 5, wherein the water soluble species comprise charged species and neutral species and the ratio by weight of the total amount of charged species to the total amount of neutral species in the soaking liquid is in a range of 20:100 to 90:100.

7. The process of claim 1, wherein the soaked ligno-cellulosic biomass stream before separation step e) has a free liquid and the percent amount of the free liquid is less than a value of 20% by weight of the soaked ligno-cellulosic biomass stream.

8. The process of claim 7, wherein the soaked ligno-cellulosic biomass stream before separation step e) is substantially void of the free liquid.

9. The process of claim 7, wherein at least a portion of the free liquid of the soaked lignocellulosic biomass stream is drained before separation step e).

10. The process of claim 8, wherein at least a portion of the free liquid of the soaked lignocellulosic biomass stream is drained before separation step e).

11. The process of claim 7, wherein the soaked ligno-cellulosic biomass stream is separated by means of a compression screw.

12. The process of claim 1, wherein at least a portion of the water insoluble contaminants are separated from the lignocellulosic biomass in the extraction vessel.

13. The process of claim 1, wherein a portion of the extraction solution is discarded from the process, and the total amount of discarded extraction solution per Kg of ligno-cellulosic biomass is less than a value 5 l/Kg.

14. The process of claim 1, wherein the ratio by weight of the ligno-cellulosic biomass present in the extraction vessel to the extraction liquid in the extraction vessel is less than a value of 1:1000.

15. The process of claim 12, wherein the temperature of the extraction solution is in a range of 30° C. to 100° C.

16. The process of claim 14, wherein the ligno-cellulosic raw biomass stream resides in the extraction vessel for a residence time which is in a range of 30 seconds to 300 minutes.

17. The process of claim 15, wherein the ligno-cellulosic raw biomass stream resides in the extraction vessel for a residence time which is in a range of 30 seconds to 300 minutes.

18. The process of claim 1, wherein the ratio of the raw ligno-cellulosic biomass stream flow in Kg/hour on a dry basis to the optional rinse solution stream in Kg/hour is less than 1:20.

19. The process of claim 18, wherein the temperature of the optional rinse solution stream is greater than or equal to the temperature of the extraction solution.

20. The process of claim 1, wherein the moisture content of the ligno-cellulosic biomass stream is a value in a range 40% to 75%.

* * * * *